US010451863B2

(12) United States Patent
Kavusi et al.

(10) Patent No.: US 10,451,863 B2
(45) Date of Patent: Oct. 22, 2019

(54) INTERPOSER FOR INTEGRATION OF MULTIPLE IMAGE SENSORS

(71) Applicant: VERILY LIFE SCIENCES LLC, Mountain View, CA (US)

(72) Inventors: Sam Kavusi, Menlo Park, CA (US); Brian M. Pepin, Oakland, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 237 days.

(21) Appl. No.: 15/230,115

(22) Filed: Aug. 5, 2016

(65) Prior Publication Data

US 2018/0039064 A1 Feb. 8, 2018

(51) Int. Cl.
*A61B 1/05* (2006.01)
*H04N 5/225* (2006.01)
(Continued)

(52) U.S. Cl.
CPC ...... *G02B 23/2484* (2013.01); *A61B 1/00096* (2013.01); *A61B 1/00193* (2013.01);
(Continued)

(58) Field of Classification Search
CPC ....... A61B 1/05; A61B 1/051; A61B 1/00188; A61B 1/00193; H04N 5/2254;
(Continued)

(56) References Cited

U.S. PATENT DOCUMENTS

| 4,760,440 A | * | 7/1988 | Bigler | ............. H01L 23/06 257/680 |
| 5,418,566 A | * | 5/1995 | Kameishi | ............. A61B 1/042 348/294 |

(Continued)

FOREIGN PATENT DOCUMENTS

KR    101084689 B1 *  11/2011   ....... H01L 27/14618

OTHER PUBLICATIONS

PCT/US2017/044978, International Search Report and Written Opinion of the International Searching Authority, dated Nov. 9, 2017, 12 pages.
(Continued)

*Primary Examiner* — John P Leubecker
(74) *Attorney, Agent, or Firm* — Christensen O'Connor Johnson Kindness PLLC

(57) ABSTRACT

Apparatuses and methods for an interposer for integration of multiple image sensors are disclosed herein. An example apparatus includes an interposer including laterally spaced first and second windows, and first and second image sensors disposed on the interposer over the first and second windows, respectively. The interposer including conductive conduits formed in or on to provide electrically conductive paths there through with the first and second image sensors coupled to the conductive conduits. The first and second image sensors laterally spaced by a gap, and an active area of the first and second image sensors to receive incident light through the respective first and second windows, where a perspective of the first image is different than a perspective of the second image sensor based at least in part on the gap.

19 Claims, 8 Drawing Sheets

(51) Int. Cl.
*H01L 27/146* (2006.01)
*G02B 23/24* (2006.01)
*A61B 1/00* (2006.01)
*A61B 1/06* (2006.01)
*A61B 1/045* (2006.01)
*H04N 13/239* (2018.01)

(52) U.S. Cl.
CPC .......... *A61B 1/00197* (2013.01); *A61B 1/045* (2013.01); *A61B 1/05* (2013.01); *A61B 1/051* (2013.01); *A61B 1/0646* (2013.01); *G02B 23/2415* (2013.01); *H01L 27/14618* (2013.01); *H04N 5/2253* (2013.01); *H04N 5/2254* (2013.01); *H04N 5/2257* (2013.01); *H04N 5/2258* (2013.01); *H04N 13/239* (2018.05); *A61B 1/0011* (2013.01); *H04N 2213/001* (2013.01)

(58) Field of Classification Search
CPC ............... H04N 5/2258; H04N 5/2257; H04N 2005/2255; H01L 27/14618; H01L 27/1469; H01L 27/14625; G02B 23/2484
See application file for complete search history.

(56) References Cited

U.S. PATENT DOCUMENTS

| | | | |
|---|---|---|---|
| 5,744,379 A * | 4/1998 | Mandai | H01L 23/5381 257/E21.705 |
| 8,891,511 B2 | 11/2014 | Taylor et al. | |
| 9,123,555 B2 | 9/2015 | Crisp et al. | |
| 9,276,140 B1 * | 3/2016 | Tam | H01L 31/02002 |
| 2002/0007110 A1 * | 1/2002 | Irion | A61B 1/00181 600/170 |
| 2004/0012698 A1 * | 1/2004 | Suda | H01L 27/14618 348/315 |
| 2004/0167378 A1 | 8/2004 | Ando | |
| 2005/0236708 A1 * | 10/2005 | Farnworth | H01L 27/14618 257/723 |
| 2006/0202318 A1 | 9/2006 | Satou et al. | |
| 2010/0002107 A1 * | 1/2010 | Harazono | H01L 27/14618 348/294 |
| 2010/0084726 A1 * | 4/2010 | Lee | H01L 27/14618 257/432 |
| 2011/0086461 A1 * | 4/2011 | Bolis | G02B 13/0085 438/65 |
| 2011/0245605 A1 * | 10/2011 | Jacobsen | A61B 1/015 600/109 |
| 2012/0019624 A1 * | 1/2012 | Park | H04N 5/2253 348/47 |
| 2012/0211852 A1 * | 8/2012 | Iwafuchi | H01L 27/14618 257/435 |
| 2013/0285185 A1 * | 10/2013 | Park | H01L 27/14618 257/434 |
| 2013/0316487 A1 * | 11/2013 | de Graff | H01L 27/14683 438/66 |
| 2014/0055670 A1 * | 2/2014 | Hongo | H04N 5/2253 348/374 |
| 2014/0168510 A1 * | 6/2014 | Hamada | H01L 27/14618 348/374 |
| 2014/0225212 A1 * | 8/2014 | Kaschner | H01L 25/042 257/443 |
| 2014/0252657 A1 * | 9/2014 | Liu | H01L 25/105 257/782 |
| 2014/0307059 A1 * | 10/2014 | Haddad | G01B 11/026 348/47 |
| 2014/0340575 A1 * | 11/2014 | Kim | G02B 26/0875 348/374 |
| 2014/0375876 A1 * | 12/2014 | Ikemoto | H05K 1/182 348/373 |
| 2015/0028187 A1 * | 1/2015 | Jin | H01L 27/14625 250/208.1 |
| 2015/0219878 A1 * | 8/2015 | Kim | H04N 5/2254 348/345 |
| 2015/0255426 A1 | 9/2015 | Son et al. | |
| 2015/0358517 A1 * | 12/2015 | Ikemoto | H01L 27/14618 29/832 |
| 2016/0006913 A1 * | 1/2016 | Kettunen | H04N 5/2258 348/374 |
| 2016/0049439 A1 | 2/2016 | Yanagita et al. | |
| 2016/0173744 A1 * | 6/2016 | Kim | H01L 27/14618 348/208.99 |
| 2016/0366313 A1 * | 12/2016 | Chang | H04N 5/2252 |
| 2017/0064172 A1 * | 3/2017 | Vittu | H04N 5/2253 |
| 2017/0094183 A1 * | 3/2017 | Miller | H04N 5/23296 |
| 2017/0155807 A1 * | 6/2017 | Zhang | H04N 5/2252 |
| 2018/0009141 A1 * | 1/2018 | Wang | G02B 3/0075 |
| 2018/0205857 A1 * | 7/2018 | Chan | H01L 31/00 |

OTHER PUBLICATIONS

International Search Report and Written Opinion from the International Searching Authority dated Jan. 18, 2018 for International Application No. PCT/US2017/044978, filed Aug. 1, 2017, 17 pages.

* cited by examiner

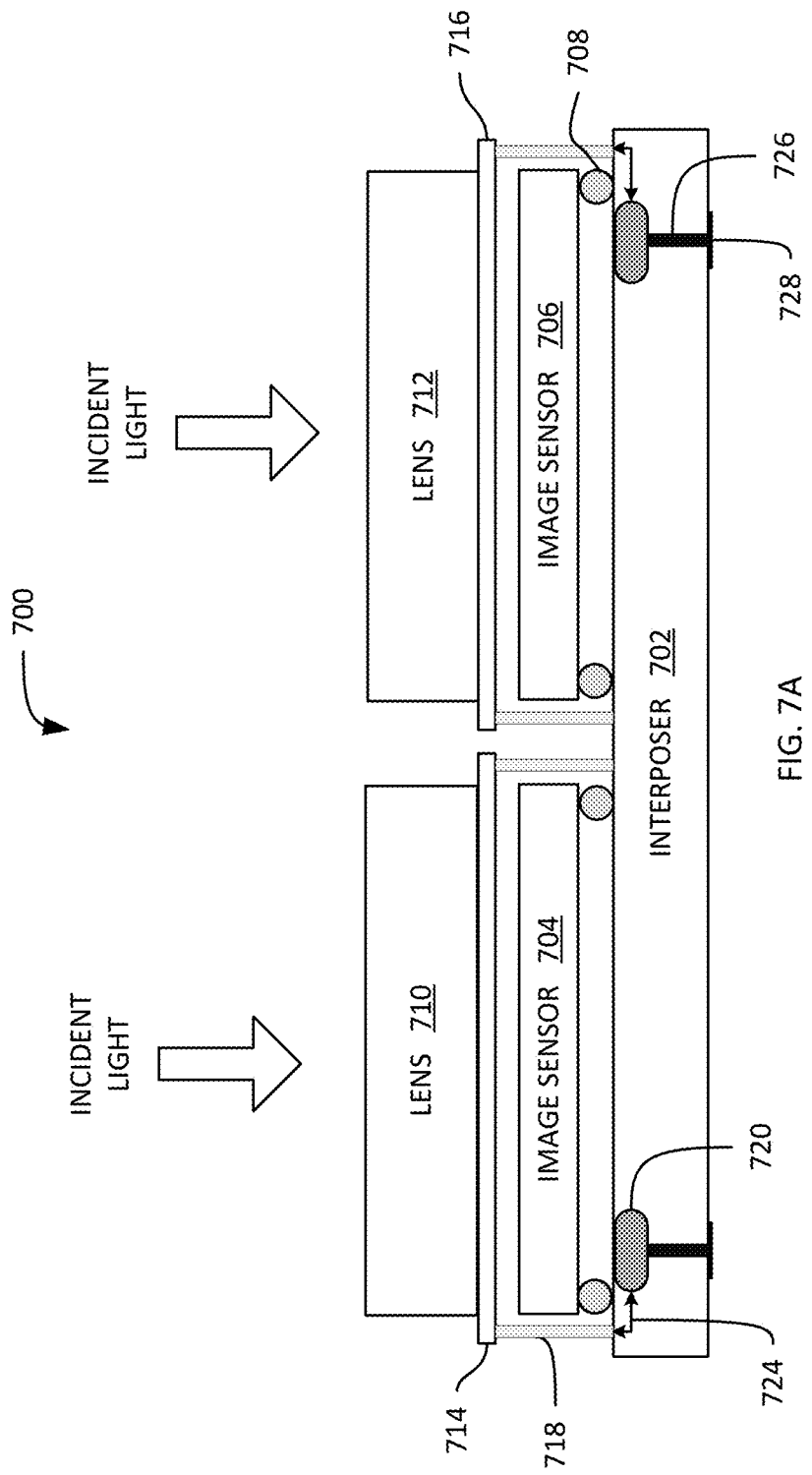

INTERPOSER FOR INTEGRATION OF MULTIPLE IMAGE SENSORS

TECHNICAL FIELD

This disclosure relates generally to imaging sensors, and in particular but not exclusively, relates to endoscopic imaging sensors.

BACKGROUND INFORMATION

Endoscopy allows a physician to view organs and cavities internal to a patient using an insertable instrument, which provides a valuable tool for making diagnoses without needing to guess or perform exploratory surgery. The insertable instruments, sometimes referred to as endoscopes, but may also be called borescopes, have a portions, such as a tube, that is inserted into the patient and positioned to be close to or inside an organ or cavity of interest. The endoscopes use various image processing techniques to provide the physician with as natural a view as possible. For example, the views provided by an endoscope may be capable of providing a natural feeling field and depth of view to emulate a physician seeing with her own eyes, for example.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIGS. 7A and 7B are block diagrams of example imaging sensor systems 700 and 750, respectively, in accordance with an embodiment of the present disclosure.

DETAILED DESCRIPTION

Figure 1:
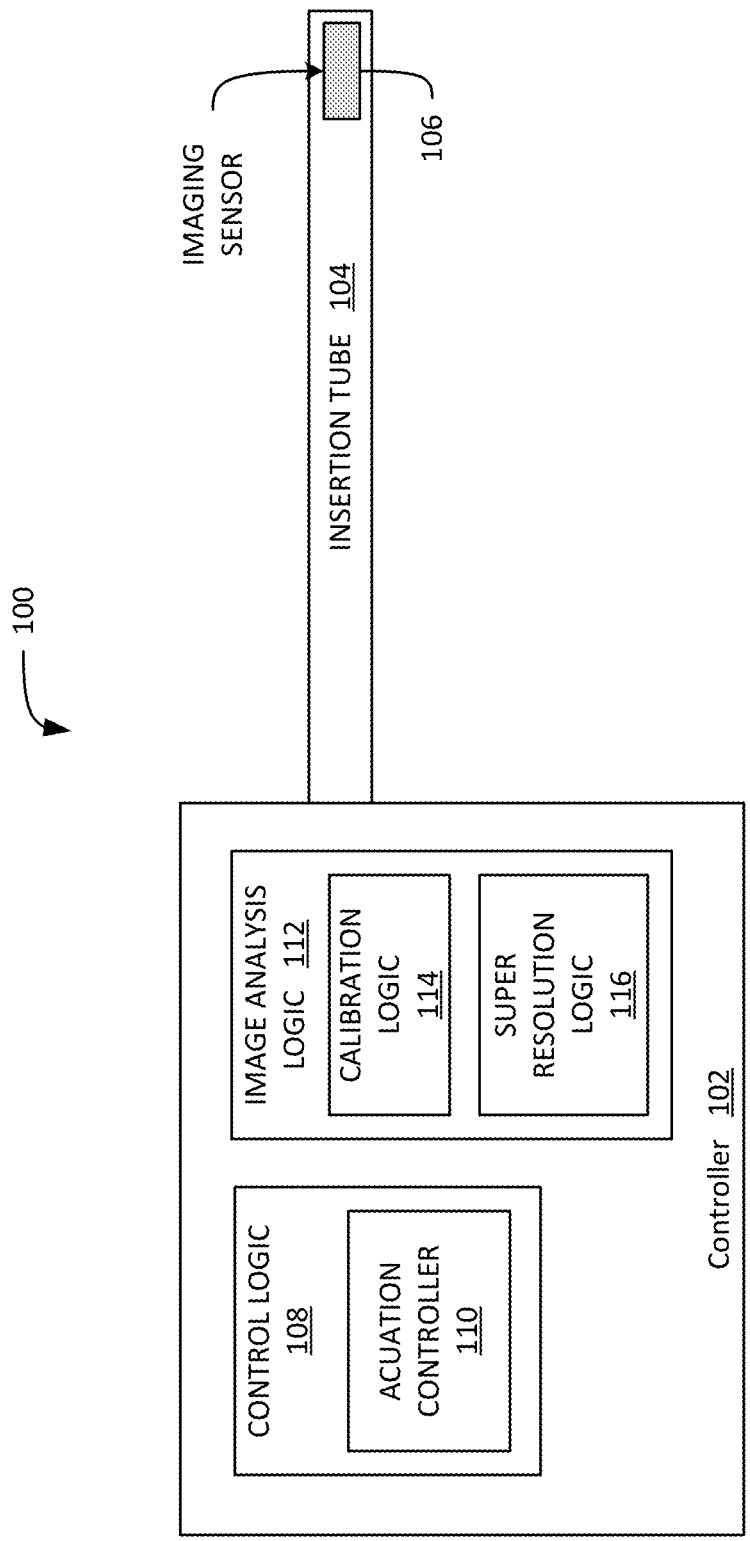
FIG. 1 is a block diagram of an endoscope in accordance with an embodiment of the disclosure.

Embodiments of a system and method for an endoscope imaging system having multiple image sensors disposed on an interposer are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Endoscopes are devices physicians use to view inside of patients without the need to perform exploratory surgery. In general, endoscopes are imaging devices with insertion tubes that are inserted into a patient through (small) incisions, where the imaging device provides views from a tip of the insertion tube and displays the view, for example, on a monitor for the physician. The tip being the distal end of the insertion tube. The imaging may conventionally provide a stereoscopic view of an area of interest so that a more natural image is provided to the viewer. To generate the stereoscopic view, endoscopes conventionally include multiple image sensors, two for example, where each image sensor provides an image of the area of interest from a slightly different perspective. The difference in perspective is intended to emulate the different perspective of human eyes.

Over time, endoscopes have gone from using image sensors at a base station, with the image sensors coupled to the tip of the insertion tube via optics, to placement of the image sensors at the tip of the insertion tube. The image sensors may have migrated to the tip of the endoscope to reduce complexities long, flexible optics may introduce into the image and the image processing. Yet, migrating the image sensors to the tip of the insertion tube has encountered its own complexities. For example, shrinking the diameter of the endoscope has become desirable for a host of reasons, e.g., a desire for smaller incisions, placement of endoscopes into smaller areas, etc., but shrinking the diameter may be limited by the size of the image sensing electronics and optics located at the tip of the insertion tube. The image sensing electronics may experience thermal problems due to the tip placement as well.

In general, endoscope image sensors may need to be precisely positioned with respect to one another in order to maintain clear stereoscopic images. The positioning and alignment may relate to a lateral spacing between the image sensors and further related to a relative focus of each image sensor. Focus of the image sensors may refer to an active area, e.g., pixel array, being incident with a focal plane of respective optics. However, as the endoscopic imaging sensors are decreased in size, the precise positioning required to maintain the desired stereoscopic views may become more difficult to maintain. The difficulty in maintaining alignment may in part be due to fabrication, manufacturing variability, and operating environment. Changes in the operating environment may cause alignment issues, which may adversely affect the stereoscopic image quality. For example, as the tip of an endoscope heats up due to use and placement within a cavity, the temperature of the environment may cause the components within the tip to expand or warp, which may cause the image sensors to become misaligned. For example, if the base to which the image sensors are mounted warps or expands, which may be different than an amount of warp or expansion by the image sensors, then the relative difference in expansion/warp may cause misalignment between the image sensors and between the image sensors and their respective optics. As such, a technique is desired to provide relative precise positioning of multiple imaging sensors at least with respect to one another, and maintenance of the positioning in a changing operating environment.

One technique to address the above problem is to dispose multiple image sensors on a single interposer. Based at least in part on self-alignment techniques, the interposer may allow for finer placement of the image sensors with respect to each other. Additionally, by utilizing an interposer of similar materials as that of the image sensors, thermal expansion mismatch between the components may be reduced or eliminated. As such, any temperature changes experienced by an imaging sensor, e.g., the combination of the interposer and image sensors, placed in a tip of an endoscope may not affect the relative location of the multiple image sensors with respect to one another and/or with respect to optics of the imaging sensor.

Additionally, actuators may be disposed between the interposer and each of the multiple imaging sensors. The actuators may allow each image sensor to be manipulated in two or three dimensions, which may allow each image sensor to be physically moved with respect to one another and/or a respective lens. Physically moving the image sensors with respect to the lens may also allow for maintaining the optical distance between the lens and the image sensor, enhanced calibration, and for implementing super resolution, for example.

FIG. 1 is a block diagram of an endoscope 100 according to an embodiment of present disclosure. The endoscope 100 includes controller 102, insertion tube 104, and an imaging sensor 106. The endoscope system 100 may provide images captured by the imaging sensor 106 to a user via the controller 102, where the imaging sensor 106 is located at a distal end of the insertion tube 104, which is inserted into a patient to view a region of interest, for example. While not shown, the user may be able to manipulate the distal end of the insertion tube so to point optics of the imaging sensor 106 toward a region of interest. In some embodiments, the imaging sensor 106 may include multiple image sensors laterally displaced from one another so that the perspective of each image sensor is different. In some embodiments, a physical location of each image sensor may be changed with respect to one another and/or with respect to optics. The controller 102 may combine captured images to provide a stereoscopic view of the region of interest.

The imaging sensor 106, based on control signals received from the controller 102, may obtain images, still or video, and may provide the images to the controller 102 in response. The imaging sensor 106 and the controller 102 may be electrically coupled via wires or wirelessly. The controller 102 may perform some image processing on the images to generate a stereoscopic image, which may then be provided to a viewer via a display (not shown) for example, or saved to a mass storage device (not shown).

The illustrated embodiment of the controller 102 is shown to include control logic 108, actuation control 110, image analysis logic 112, calibration logic 114, and super resolution logic 116. In operation, the controller 102 may provide illumination (not shown) to the tip of the insertion tube 104 via fiber optics, for example, to illuminate a region of interest. In general, the controller 102 controls the operation of the endoscope 100, which may be in response to user input.

Control logic 108 may include circuit logic that coordinates the operation of the other components of endoscope 100. For example, control logic 108 may control the operation of the various aspects of the endoscope 100 through coordination of the various other modules included in the controller 102. Controller 102 may be implemented as hardware logic (e.g., application specific integrated circuit, field programmable gate array, etc.), software/firmware logic executed on a general purpose microcontroller, or a combination of both hardware and software/firmware logic.

Actuation controller 110 may be software, hardware, or a combination thereof for the control of actuators included in the imaging sensor 106. The actuators may move a respective image sensor included in the imaging sensor 106. The movement of the image sensors may be performed for a variety of reasons, such as focus adjust, calibration, and super resolution. In some embodiments, the actuation controller 110 may provide control signals based on one or more inputs from the calibration logic 114, or the super resolution logic 116.

Image analysis logic 112 may perform analysis of images received from the imaging sensor 106, and may also generate the stereoscopic images provided by the endoscope 100 based on multiple images captured by the imaging sensor 106. The image analysis logic 112 may provide one or more inputs to the control logic 108 and/or the actuation controller 110 as feedback for controlling the imaging sensor 106, for example.

Calibration logic 114 may control image capture calibration and imaging set up for the imaging sensor 106. The control logic 108 may initiate calibration logic 114 to perform one or more calibration processes with the imaging sensor 106. The calibration logic 114, using the image analysis logic 112, may cause the actuation controller 110 to move one or more image sensors of the imaging sensor 106 to adjust the quality of the images captured by the imaging sensor 106 and, by extension, the quality of the stereoscopic images provided by the endoscope 100. For example, the calibration logic 114 may provide inputs to the actuation controller 110 to cause one or more image sensors of the imaging sensor 106 to be physically moved.

Super resolution logic 116 may control the generation of super resolution images, for example. Super resolution, in general, is the process of acquiring multiple images by an image sensor with the image sensor in a different lateral location (x and/or y direction) for each image. The multiple images may then be combined to provide an image that has better resolution than any of the single multiple images alone. Accordingly, super resolution logic 116 may coordinate with actuation control logic 110 and image analysis logic 112 when performing super resolution. As such, for each image used in the generation of a super resolution image, the super resolution logic 110 may cause the actuation control logic 110 to move the one or more image sensors in a lateral direction, x, y, or a combination thereof, the imaging sensor 106 to acquire an image with each of the one or more image sensors, and the image analysis logic 112 to grab and store each image acquired at each location. After all images have been acquired, which can be from two or more, the image analysis logic 112 may combine the images according to the super resolution logic 116 to generate the super resolution images and/or a super resolution stereoscopic image.

Insertion tube 104 may provide a means for inserting the imaging sensor 106 into a patient to view the region of interest. The insertion tube 104 may provide electrical connections between the controller 102 and the imaging sensor 106, and illumination. In some embodiments, the insertion tube 104 may include mechanical actuation so that at least the tip may be articulated. For example, a physician may manipulate the mechanical actuators to move the tip in a desired direction. In some embodiments, the insertion tube 104 may be actuated by electrically controlled actuators, which may also be controlled by the controller 102.

Imaging sensor 106 may be located at the distal end of the insertion tube, e.g., the tip, and may acquire one or more images in response to control signals provided by the controller 102. The controller 102 may receive the one or more images and generate a stereoscopic image based thereon. The imaging sensor 102 may at least include two or more image sensors, such as CMOS image arrays, and respective optics, such as lenses or lens barrels. In some embodiments, the imaging sensor 106 may include two image sensors. The image sensors may be disposed on a substrate, such as an interposer, and separated from one another by a desired gap so that each image sensor has a different perspective. Further, each image sensor may be positioned so that an active area, e.g., pixel array, is incident with a focal plane of their respective optics. In some embodiments, the image sensors may be articulated in one, two or three directions so that each image sensor may be moved in relation to at least one of the other image sensors and/or the focal plane of their respective optics.

In general, it may be desirable that the active area of the image sensors to be static with regards to their relative position so to preserve the quality of the stereoscopic image. To provide stereoscopic images, the image analysis logic 112 may interpolate between pixel data, which may be affected by the relative location of pixels of the two imagers. More specifically, if pixels of one image sensor move with respect to the pixels of the other image sensor, the interpolation may be affected, which may in turn affect the quality of the stereoscopic images provided by the endoscope 100. Thus, by mounting the multiple image sensors on an interposer to maintain the relative spacing between the active areas of the image sensors, the image quality may at least be maintained.

The image sensors may be arranged in a number of ways, such as one a same side of the interposer, on opposite sides of the interposer such that the interposer is between the image sensors. In some embodiments, an actuator may be arranged between the image sensor and the interposer. In such an embodiment, the actuator may move, e.g., translate, the image sensor laterally or rotationally. For example, the image sensor may be moved in at least two directions, if not three directions, so that a relative position between the image sensors is maintained, and to align the active areas with the focal plane of their respective optics. Additionally, the interposer may have one or more through conductors formed therein to provide electrical connections through the interposer so that the controller 102, for example, may be electrically coupled to the one or more image sensors disposed on the interposer.

While FIG. 1 shows the various controlling features, such as the actuation controller 110, the calibration logic 114, and the super resolution logic 116, as being included in the controller 102. These depictions, however, are not mean to be limiting to the present disclosure, and various other arrangements are contemplated. The arrangement of the controller 102 as shown is for illustrative purposes only. In some embodiments, some, or even all, of the controlling features that may be associated with the image sensor 106 may be located at the tip of the insertion tube 104 in proximity with the image sensor 106. For example, the actuation controller 110 may be included with the image sensor 106.

Figure 2:
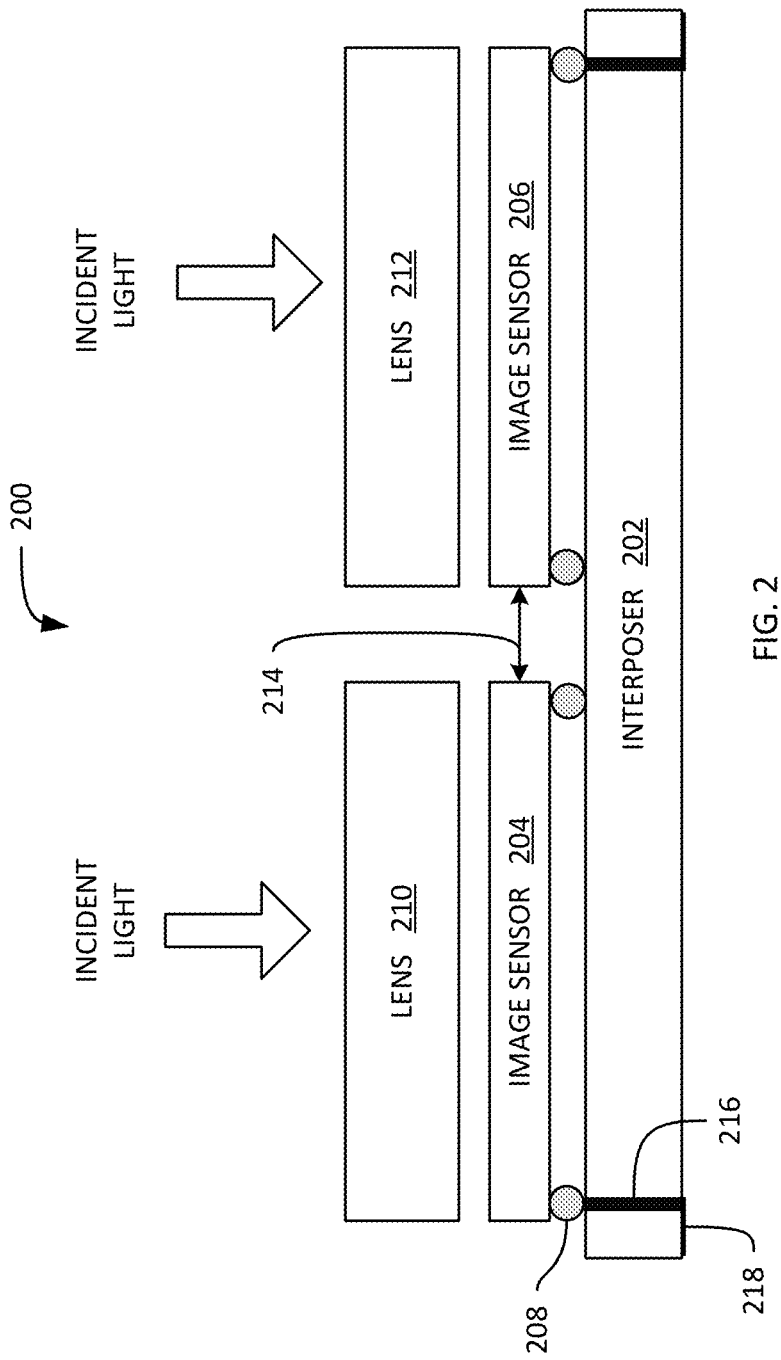
FIG. 2 is an illustrative imaging sensor system in accordance with an embodiment of the disclosure.

FIG. 2 is a block diagram of an example imaging sensor system 200 in accordance with at least one embodiment of the present disclosure. The imaging sensor system 200, for example, may be used for the imaging sensor 106 of FIG. 1. In general, the imaging sensor system 200 may include an interposer, a plurality of image sensors, and a plurality of lenses, with each lens associated with a respective image sensor. For sake of clarity, the imaging sensor system 200 will be discussed as having two image sensors, and two respective lenses, but the number of imaging sensors and lenses is a non-limiting aspect of the present disclosure. As such, the illustrated embodiment of the imaging sensor system 200 is shown to include an interposer 202, image sensors 204 and 206, and lenses 210 and 212.

The lenses 210 and 212 may focus an image onto an active area of their respective image sensors 204 and 206. Each of the lenses 210 and 212 may be a lens barrel that includes a number of lenses and various other optical components arranged to provide a desired field of view at a desired depth of view. Accordingly, each of the lenses 210 and 212 may include prisms, aspherical lenses, waveguides, concave lenses, convex lenses, polarizers, filters, and various combinations thereof. The lenses 210, 212 may have respective focal planes, which may be fixed in space due to the lenses 210, 212 being fixed in space at least with respect to their respective image sensors 204, 206. The lenses may be located at a distal end of an insertion tube, such as the insertion tube 104, such that the lenses direct incident light from the tip of the insertion tube to the active surfaces of their respective image sensors 204, 206. The incident light may form an image on the active areas of the image sensors, for example.

An optical axis of each of the lenses 210, 212 may be aligned to a central area of the active area of the image sensors 204, 206 so that the image provided by the lenses is incident within an optimal active area of the image sensors. Further, the focal plane of the lenses 210, 212 may be coincident with the active area of the image sensors 204, 206 so that images acquired by the image sensors 204, 206 are substantially in focus.

The image sensors 204, 206 may be front side or backside illuminated imaging arrays that include a plurality of pixels along with other control and timing circuits. Example imaging arrays may be CMOS-based arrays, near infrared field pixel arrays, and near infrared pixel arrays, but other image sensors fall within the scope of the present disclosure. As such, the type of image sensor is a non-limiting aspect of the present disclosure. The image sensors 204, 206 may receive light via the respective lenses 210, 212 and convert the light into an image and/or image information. The image and/or image information may be provided to an endo scope controller, such as the controller 102 for example, which may then be displayed, stored, printed, etc., for a user to review.

The interposer 202 may be used to support the image sensors 204, 206, and may further allow the image sensors 204, 206 to be precisely positioned with respect to each other. The precise position may be related both to a lateral distance between the two image sensors, and also to a plane in which the active surfaces of the two image sensors are located. A lateral distance between the two image sensors 204, 206, such as defined by gap 214, may cause the image sensors 204, 206 to have different perspectives of an object. A width of the gap 214 may determine the different viewpoints of the two image sensors 204 and 206, which may affect stereoscopic images an endoscope generates based thereon. Additionally, maintaining the width of the gap 214 during operation may be desirable so not to affect the quality of the stereoscopic image. As noted above, the lateral distance between the image sensors 204, 206, or more specifically the lateral distance between their active areas, may affect the quality of the stereoscopic images, and maintaining a constant gap may be desirable so that the quality of the stereoscopic images is not degraded due to changes in the width of the gap 214. The width of the gap, for example, may be 750 microns or less. The image sensors 204, 206 may be placed on the interposer 202 using self-aligning techniques to ensure the placement is accurately controlled and to further control the width of the gap. In some embodiments, bonds 208 may be formed using self-aligning trenches formed in bonding pad areas on both the images sensors 204, 206 and the interposer 202.

In some embodiments, it may be desirable for the interposer 202 to have physical characteristics that substantially match those of the image sensors 204, 206. For example, if the image sensors are fabricated from silicon, then it may be desirable to form the interposer 202 from silicon as well. Using silicon for the interposer and the image sensors may provide substantially equal coefficients of thermal expansion. Other examples of materials for forming the interposer 202 include germanium, germanium-silicon, and the III-V material system (e.g., GaAs, InP, InGaAs, InGaP, etc.), to name a few. However, the material used to form the interposer and/or the image sensors is a non-limiting aspect of the present disclosure, however. Due to the thermal environment the imaging sensor system 200 may experience when implemented in an endoscope system, for example, the equal expansion and contraction the interposer 202 with respect to the image sensors 204, 206, the relative location of the image sensors 204, 206 with respect to each other may substantially remain the same. As a result, the quality of the images provided by the imaging sensor system 200 may not be affected.

In some embodiments, the interposer 202 may have through conductors 216 formed therein, which may be used to provide conductive paths through the interposer 202. In some examples, the through conductors 216 may be through vias as in known in the art. The through conductors 216 may be coupled to contact pads 218 on one or more surfaces of the interposer 202, and further coupled to the image sensors 204, 206 by the bonds 208. The contact pads 218 may be located on an opposite side of the interposer 202 than the image sensors 204, 206. Yet, the location of the contact pads 218 is a non-limiting aspect of the present disclosure. In some embodiments, the through conductors 216 may be used to couple the image sensors 204, 206 to control electronics, such as the controller 102, which may be electrically coupled to the contact pads 218.

Figure 3:
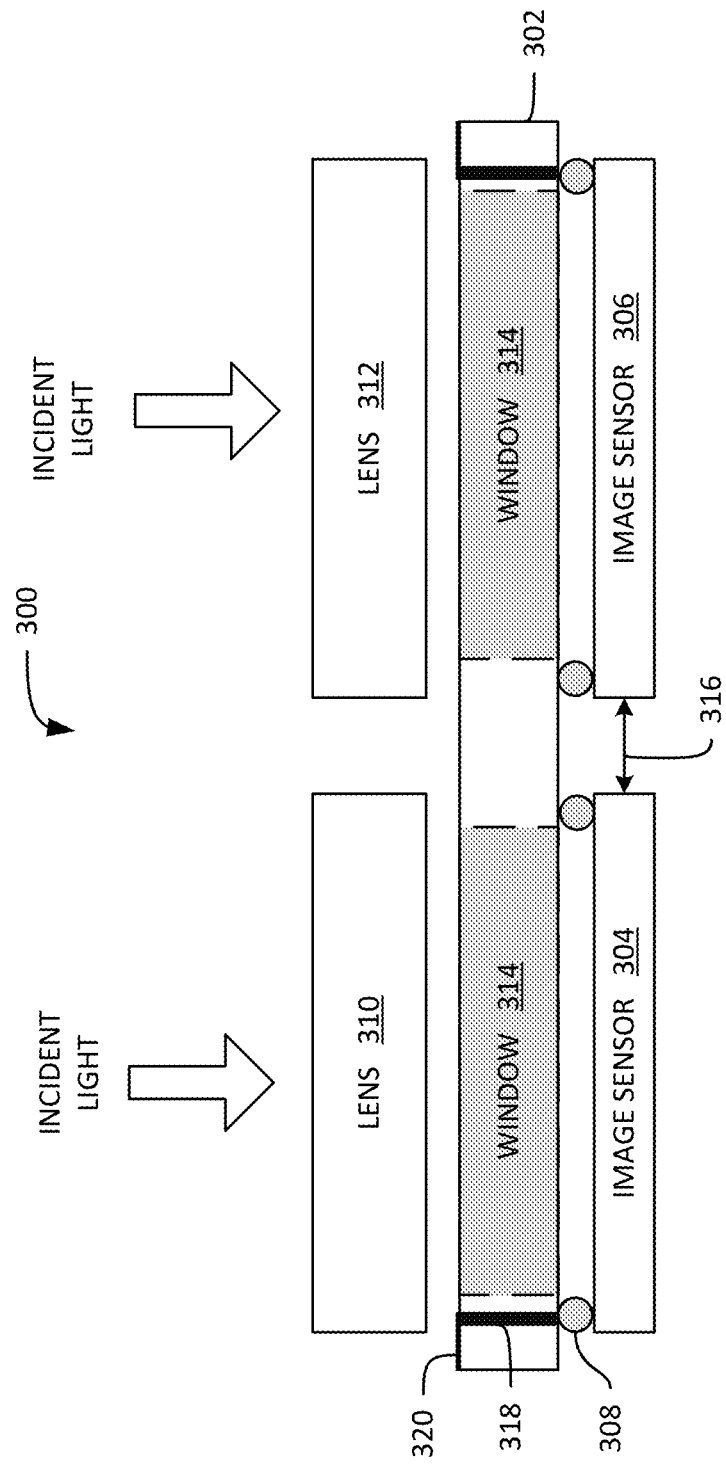
FIG. 3 is an illustrative imaging sensor system in accordance with an embodiment of the disclosure.

FIG. 3 is a block diagram of an example imaging sensor system 300 in accordance with an embodiment of the present disclosure. The imaging sensor system 300, for example, may be used for the imaging sensor 106 of FIG. 1. The imaging sensor system 300 may be similar to the imaging sensor system 200 in certain aspects, but an interposer of the imaging sensor system 300 may have windows formed therein. The illustrated embodiment of the imaging sensor system 300 is shown to include interposer 302, image sensors 304 and 306, and lenses 310 and 312. The imaging sensor 300 may acquire images with the image sensors 304, 306 and provide the images to a controller of an endoscope, for example. The image sensors 304, 306 and the lenses 310, 312 may be substantially similar to the image sensors and lenses discussed above with respect of FIG. 2, and in the interest of brevity, they will not be discussed in detail with respect to FIG. 3.

The interposer 302 may have two windows formed therein, such as windows 314. The windows may have been formed from etching, such as wet etching, dry etching, or laser ablation. The windows 314 may allow light to pass through the interposer before reaching an active area of the image sensors 304, 306. To further illustrate, the windows may be apertures for the image sensors 304, 306, for example. The lenses 310, 312 may be positioned above the windows 314 on the other side, e.g., opposite side, of the interposer 302 than their respective image sensors 304, 306 are positioned.

The image sensors 304, 306 may be formed on, e.g., attached to, a same side of the interposer 302 by bonds 308. The bonds 308 may include grooves etched into bonding pad surfaces of both the image sensors 304, 306 and the interposer 302. The grooves may provide a self-aligning attachment mechanism that provides precise placement of the image sensors 304, 306 at least with respect to each other. The precise placement may cause the relative lateral spacing of the image sensors to be spaced by a gap 316. As with the gap 214, the gap 316 may assist in establishing the different perspectives of the image sensors 304, 306 such that a stereoscopic image may be generated based on images acquired by the image sensors.

The bonds 308 may be coupled to through conductors 318, which may provide electrical connections for the image sensors 304, 306 to contact pads 320. External electronics, such as a controller and/or image processor, may communicate with the image sensors 304, 306 via the contract pads 318, for example.

Additionally, the lenses 310, 312 may be arranged over the windows 314 so that an optical axis of the lenses provide incident light onto an active surface of the image sensors 304, 306, respectively. The light provided by the lenses 310, 312 may propagate through respective windows 314 before arriving at the image sensors 310, 312. Further, the lenses may be placed at a distance from the active surface of the image sensors 304, 306 so that a focal plane of the lenses is coincident with the active surfaces. Arrangement of the lenses as such may provide a focused image to the active surfaces of the respective image sensors.

Figure 4:
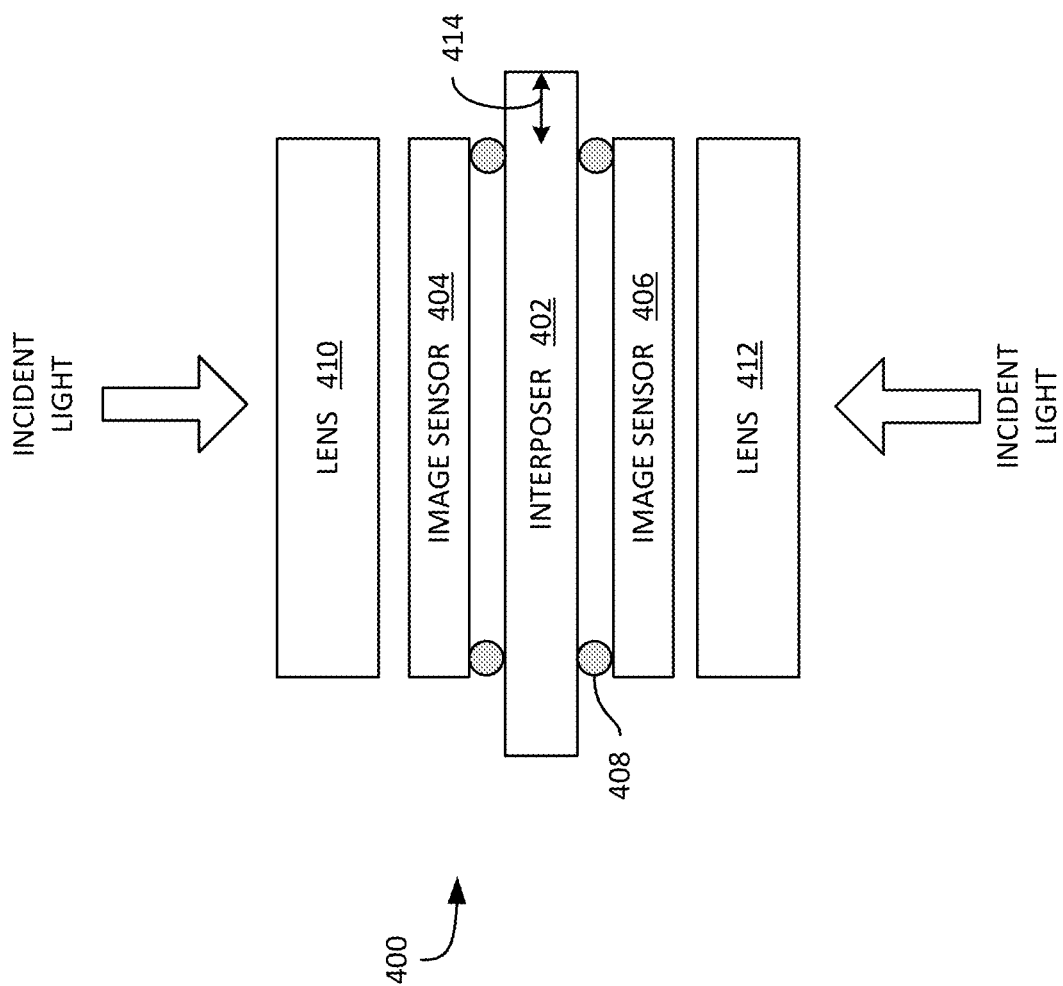
FIG. 4 is an illustrative imaging sensor system in accordance with an embodiment of the disclosure.

FIG. 4 is a block diagram of an example imaging sensor system 400 in accordance with an embodiment of the present disclosure. Imaging sensor system 400 may be an example of an image sensor 106. The illustrated embodiment of the image sensor system 400 includes interposer 402, image sensors 404 and 406, lenses 410 and 412. The image sensors 404, 406 may be mounted to the interposer 402 by self-alignment bonds 408. Although not shown in FIG. 4, the imaging sensor system 400 may have through conductors formed in the interposer 402, as well as contact pads formed on a surface of the interposer 402. The through conductors and contact pads to provide electrical connections with the image sensors 404, 406 to external electronics, for example. The imaging sensor system 400 may be similar to the imaging sensor 200 in most aspects except that the image sensors 404, 406 are located on opposite sides of the interposer 402. While a lateral gap between the image sensors 404 and 406 may not be present as it is in FIGS. 2 and 3, the placement of the image sensors 404 and 406 on the interposer 402 may be performed so that an active area of each is positioned substantially similar with respect to a side of the interposer 402. For example, the image sensors may be positioned on the interposer 402 so that a side is a distance 414 from an edge of the interposer 402.

Figure 5:
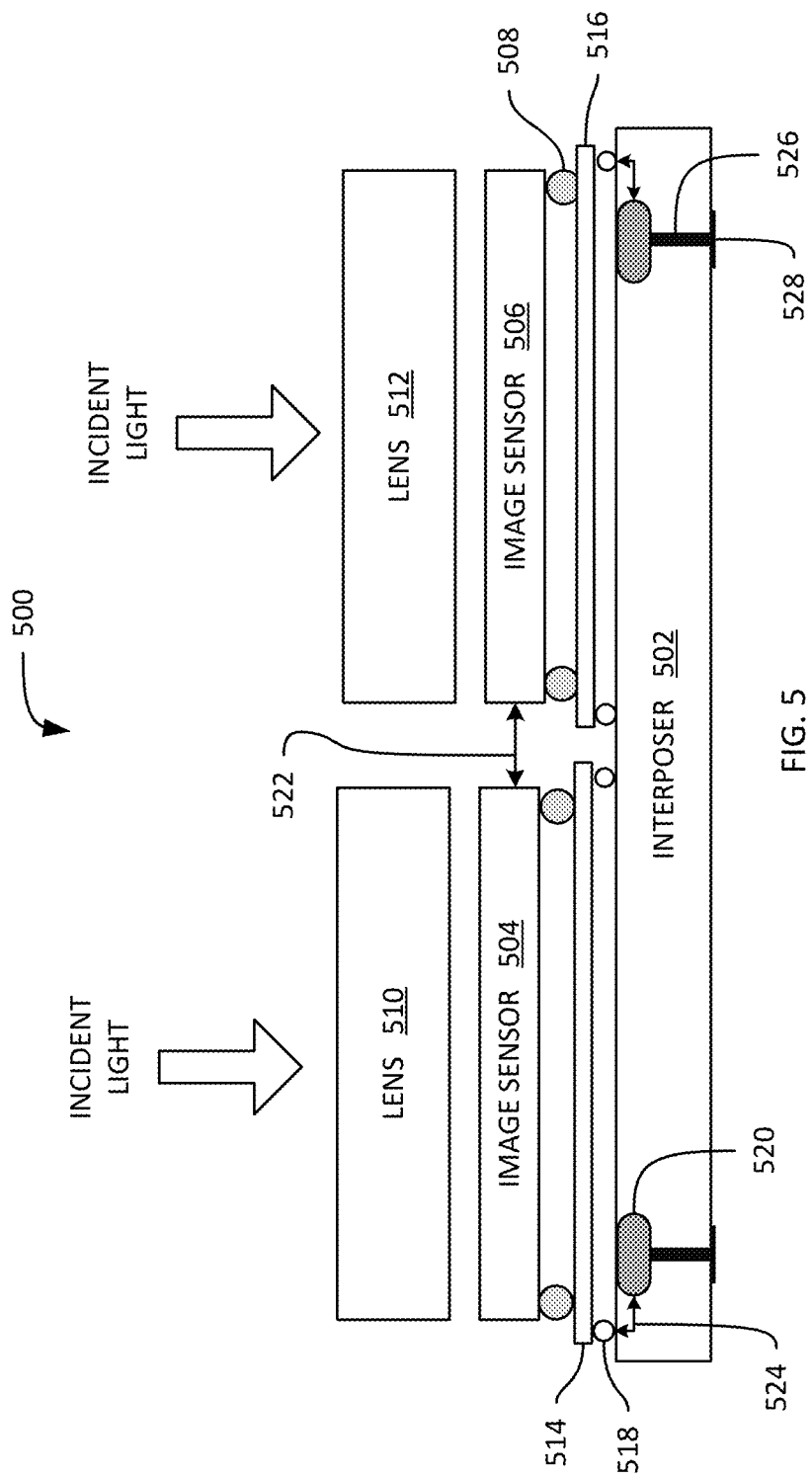
FIG. 5 is an illustrative imaging sensor system in accordance with an embodiment of the disclosure.

FIG. 5 is a block diagram of an example imaging sensor system 500 in accordance with an embodiment of the present disclosure. The imaging sensor system 500 may be an example of the imaging sensor 106 of FIG. 1. The imaging sensor system 500 may be similar to the imaging sensor systems 200 and 300 in some aspects but further include an actuator positioned between the interposer and each image sensor. The illustrated embodiment of the imaging sensor system 500 includes interposer 502, image sensors 504 and 506, lenses 510 and 512, and actuators 514 and 516. The actuators 514, 516 may move their respective image sensors 504, 506 in two, three, or four directions in response to control signals. For example, the actuators 514, 516 may move their respective image sensors 504, 506 laterally, rotationally, and/or vertically. The control signals may be electrostatic, magnetic, or thermal, for example. The image sensors 504, 506 may be moved based on a desired operation. For example, if one or both of the image sensors 504, 506 is determined to be out of a focal plane of their respective lens 510, 512, then the image sensor 504, 506 determined to be out of focus may be moved by the respective actuator 514, 516. Additionally, the actuators 514, 516 may reposition the image sensors 504, 506 for implementing super resolution imaging techniques. As noted, super resolution uses multiple images taken from different vantage points, then algorithmically-combines the multiple images to provide a composite image having improved resolution. This technique may be implemented on both image sensors, either simultaneously or serially, so that the stereoscopic image has improved resolution, e.g., super resolution.

The interposer 502 may include actuation controllers 520 formed therein, which may include circuits and logic for providing control signals to the actuators 514, 516. The actuation controllers 520 may be formed in the interposer 502 using standard semiconductor fabrication techniques, for example. In some embodiments, the actuation controllers 520 may be examples of the actuation controller 110. The actuation controllers 520 may be coupled to a respective actuator 514, 516 via connections 524 and 518. In some embodiments, the actuation controllers 520 may receive signals from an external controller (via through conductor 526 and contact pad 528), controller 102 for example, which may cause at least one of the actuation controllers 520 to move at least one of the actuators 514, 516. In some embodiments, the actuation controllers 520 may provide control signals to one of the actuators 514, 516 in response to feedback received directly from one of the actuators 514, 516 and/or one of the image sensors 514, 516. For example, the image sensors 504, 506 may include internal image processing that may determine whether a captured image is in focus, and, if not, may provide feedback to an actuation controller 520. The feedback may provide an amount the image is out of focus and how to move the image sensor with respect to a respective lens to adjust the focus.

The interposer 502 may be coupled to the actuators 514, 516 through connections 518. Similar to the bonds 508, the connections 518 may also be bonds formed from self-aligning ridges, and grooves that provide placement of the actuators 514, 516 on the interposer 502. Further, through conductors 526 be formed through the interposer 502 to provide electric connections to at least the actuators 520. Contact pads 528 may be formed on a surface of the interposer 502 to provide one or more external connection points to the through conductors 526, and by extension, the actuation controllers 520, and image sensors 504, 506. While not shown, a data path may exist between the contract pads 528 and the image sensors 504, 506 that may go through the actuation controllers 520, and actuators 514, 516 via the connections/bonds 518 and 508. The data path may allow data and control signals to be electrically coupled between the image sensors 504, 506 and an external controller, such the controller 102.

The contract pads 528 and the through conductors 526 may be formed using standard semiconductor manufacturing techniques, and may be formed from one or more metals. For example, the through conductors 526 may be formed in vias etched in the interposer 502, where the through conductors 526 may be deposited metal(s), such as gold, silver, nickel, chromium, copper, etc. The contact pads 528 may be similarly formed on the surface of the interposer 502.

The actuators 514, 516 may be MEMs-based devices that include voltage controlled mechanics that may move the image sensors 514, 506. The voltage controlled mechanics may use comb-like structures that move a floating piece when a voltage is applied to the comb-like structures. In some embodiments, nested mechanics may provide multiple degrees of freedom, which may translate into moving the image sensors in multiple directions.

The image sensors 504, 506 may be mounted to respective actuators 514, 516 via self-aligning bonds 508. The self-aligning bonds 508 may have been etched into bonding surfaces of the image sensors and the actuators to ensure the placement of the image sensors provides the desired lateral separation between the two image sensors. For example, gap 522 may be obtained when the self-aligning bonds 508 are used for mounting the image sensors 504, 506 to respective actuators 514, 516.

In some embodiments, the actuators 514, 516 may be used by an endoscope, such as the endoscope 100, to perform calibration. The actuators 514, 516 may, based on control signals, move their respective image sensors 504, 506 so that they each image sensor provides an image of substantially similar focus. Additionally, the actuators 514, 516 may move the respective image sensors 504, 506 so that the gap 522 is maintained at a desired width based on a stereoscopic image generated from the respective images. A quality of the stereoscopic image may be determined from a comparison of images captured by the image sensors over a period of time to determine if there is a drift in either of their perspectives. If so, one or both of the image sensors 504, 506 may be moved to obtain the desired width of the gap 522. To perform the calibration, the image sensors 504, 506 may acquire one or more respective images. The one or more respective images may be provided to a controller to determine a difference in focus and/or a drift in perspective over time, for example. Based on the difference in focus or the drift in perspective, the controller may determine which of the image sensors 504, 506 to move, and control signals indicative of a direction and amount of movement may be provided in response. In some embodiments, both image sensors 504, 506 may be moved. The movement may be in one, two or three directions so that an active area of the image sensors 504, 506 is moved with respect to one another and/or with respect to a focal plane of their respective lenses. The process may be repeated until the desired focus is obtained for both image sensors.

As noted above, super resolution includes the combination of multiple images taken from different perspectives to provide an image with enhanced resolution. The different perspective may be obtained by physically moving an image sensor in the x and y directions, for example, an acquiring an image at a number of different locations in the x-y plane. To implement super resolution, the imaging sensor system 500 may move the image sensors 504, 506 to a plurality of locations using respective actuators 514, 516 and an image of the same object may be acquired at each location. After the images are acquired, a super resolution algorithm performed by a controller, for example, may combine the images to provide the enhanced resolution image.

Figure 6:
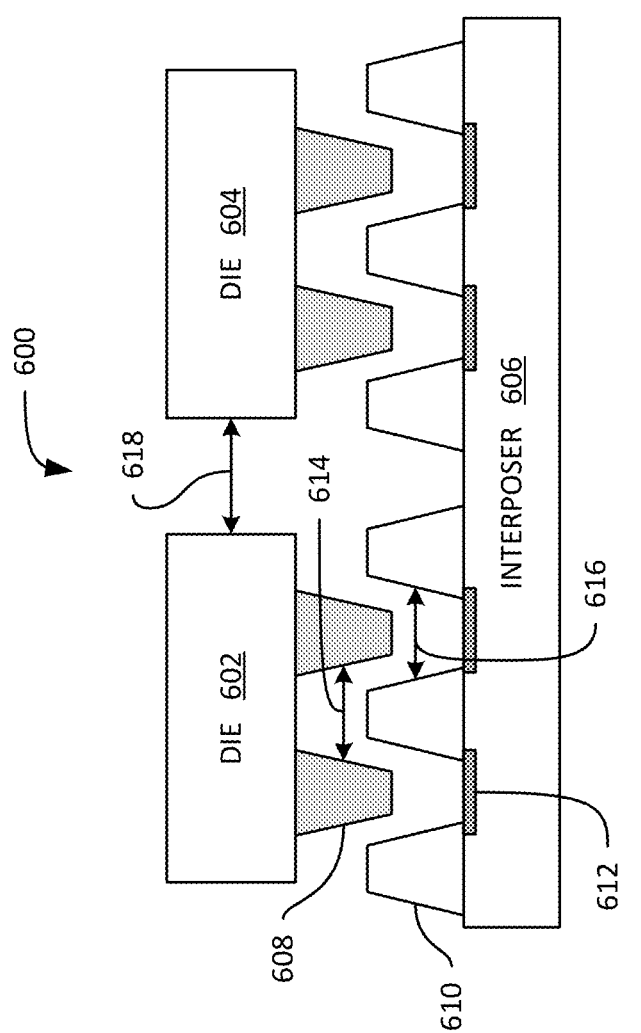
FIG. 6 is a block diagram of self-alignment bonds for mounting image sensor die to an interposer in accordance with an embodiment of the disclosure.

FIG. 6 is block diagram of self-aligning bonds 600 for mounting image sensor die to an interposer in accordance with an embodiment of the present disclosure. The self-aligning bonds 600 may be examples of the bonds 208, 308, 408, and 508. The illustrated embodiment of the self-aligning bonds 600 is show to include die 602 and 604, and interposer 606. The self-aligning bonds 600 may allow for precise placement of the die 602, 604 onto the interposer 606, and further provide precise lateral spacing of the die 602, 604.

Both of the die 602, 604 may have ridges, such as the ridges 608, formed in or on one or their surfaces. The ridges 608 may form grooves 614 with the space between the ridges 608. The ridges 608, and by extension the grooves 614, may be formed using a wet etch or a dry etch, for example. In some embodiments, the ridges 608 may be formed on an entire surface of the die 602, 604, which may result in grooves 614 formed over the entire surface. In some embodiments, the ridges 608 may be formed in small areas of the surface of the die 602, 604, which may result in grooves 614 formed only in the small areas of the surface. The ridges 608 and grooves 614 may be used for mechanically and/or electrically bonding the die 602, 604 to the interposer 606. Surfaces of the ridges 608, such as sidewalls, a top surface, or both, may be coated with a metal, such as gold, nickel, chromium, silver, etc. The metal surfaces may promote metallic bonding upon heat treatment, annealing or metal reflow for example.

The interposer 606 may have ridges 610 formed in or on one of its surfaces. The formation of the ridges 610 may result in the formation of grooves 616, which may be defined by the space between the ridges 610. The ridges 610 may be formed on an entire surface or small areas of a surface of the interposer 606. Wet or dry etching, for example, may be used to form the ridges 610. Surfaces of the ridges 610, such as sidewalls and a top surface, may be coated with one or more metals, in some embodiments. The one or more metals may be used to form metallic bonds upon heat treatment.

In or on a surface of the interposer 606 that is between the ridges 610, bonding sites 612 may be formed. The bonding sites 612 may be formed from one or more metal layers, such as gold, nickel, silver, etc., and may provide a mechanical and/or electrical bonding location for mating the die 602, 604 with the interposer 606.

The ridges 608, 610 may fit into the grooves 616, 614 to provide bonding and placement control between the die 602, 604 and the interposer 606. For example, the die 602, 604 may be placed on the interposer 606 in desired locations so that the die 602, 604 are laterally spaced apart by a gap 618. The gap 618 may be 750 microns or less, for example. After placement, the stack, e.g., die and interposer combination, may be heat treated to form metallic bonds at least where ridges 608 are in close proximity with bonding sites 612. In some embodiments, the metallic bonds are mechanical bonds, whereas in other embodiments, the metallic bonds also provide electrical connection between the die 602, 604 and the interposer 606.

Figure 7B:
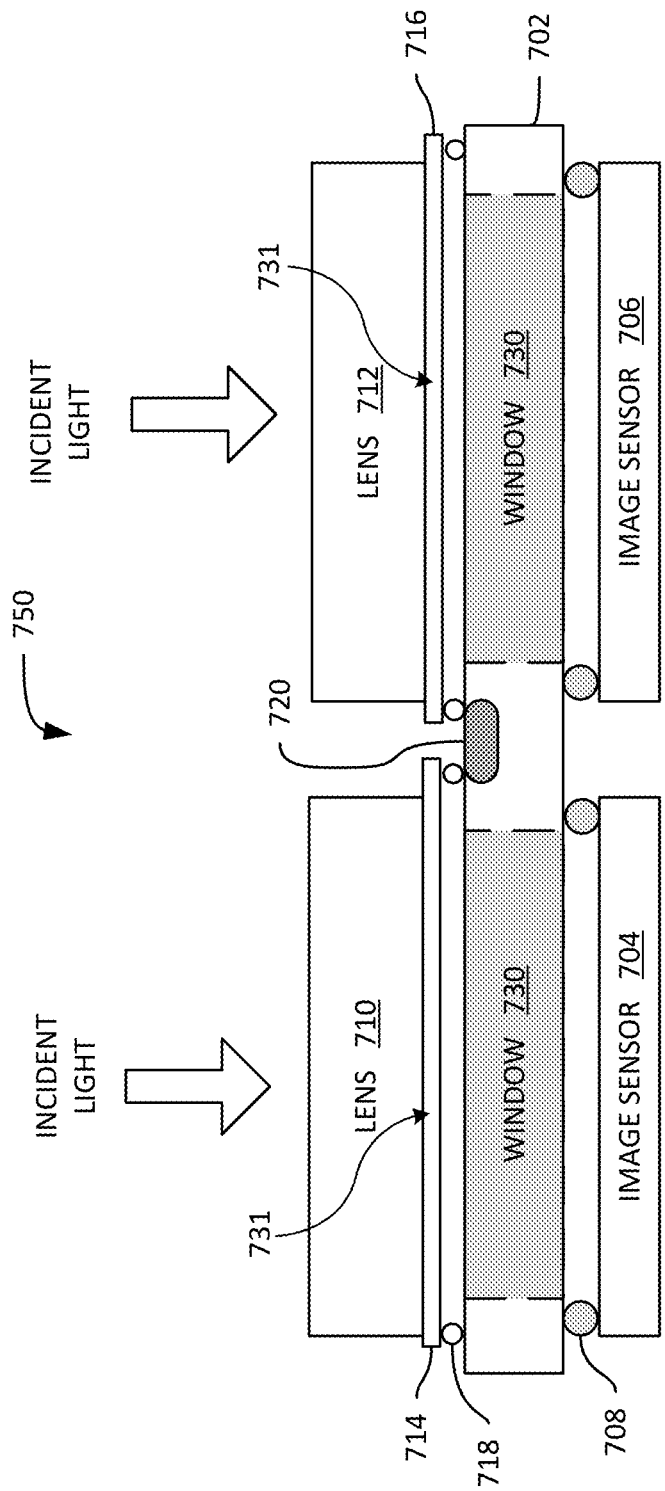

FIGS. 7A and 7B are block diagrams of example imaging sensor systems 700 and 750, respectively, in accordance with an embodiment of the present disclosure. The example imaging sensor system 700 may be similar to the imaging sensor system 500 except the actuators of the system 700 may manipulate the lenses instead of the image sensors. The illustrated embodiment of the system 700 includes interposer 702, image sensors 704 and 706, lenses 710 and 712, and actuators 714 and 716. Other than the arrangement of the components of the system 700, the components of the system 700 may be similar to the components of the system 500, and in sake of brevity, they will not be individually discussed.

The lenses 710, 712, which may be lens barrels that include a number of different optical components, may be mounted to, e.g., affixed to, respective ones of the actuators 714, 716. The lenses 710, 712 may be mounted so that they may be moved by their actuators 714, 716, such as laterally, vertically, and/or rotationally. In some embodiments, the combination of the lenses 710, 712 and the actuators 714, 716 may form a component of the system 700 that may be mounted/dismounted from the interposer 702, for example.

In general, the lenses 710, 712 may both be lens barrels that include various other optical components that provide a desired field of view at a desired depth of view. For example, each lens 710, 712 may include multiple focusing and/or magnifying lenses, one or more optical filters, one or more polarizers, one or more prisms, one or more waveguides, and combinations thereof. In some embodiments, the lenses may be convex, concave, aspherical, and combinations thereof.

The actuators 714, 716 may be coupled to the interposer 702 via connections 718. In some embodiments, the connections 718 may provide both an electrical conductive path between the interposer 702 and the actuators 714, 716, while also providing a mechanical means of mounting the actuators 714, 716 to the interposer 702 and over the image sensors 704, 706. As such, the actuators 714, 716 may act as a platform for the lenses 710, 712. In some embodiments, the lenses 710, 712 may be affixed to their respective actuators 714, 716 and mounted to be over the image sensors 704, 706, while the connections 718 provide electrical connections between the actuators 714, 716 and the interposer 702. Specifically, the connections 718 may provide an electrical connection between actuation control 720 and the actuators 714, 716. While not shown in FIG. 7A, the actuators 714, 716 may each have an aperture aligned with an optical path of the respective lenses 710, 712 that allows for the incident light to propagate through the lenses 710, 712, the actuators 714, 716, and be incident on an active area of the respective image sensors 704, 706.

The actuation control 720, similar to the actuation control 520, may provide control signals to the actuators 714, 716 via conductive path 724 in response to feedback, for example. The control signals may cause the actuators 714, 716 to move one or both of the respective lenses 710, 712. For example, the lens 710 may be moved laterally and/or vertically during a calibration routine to ensure a focal plane of the lens 710 is coincident with an active area of the image sensor 704. Further, one or both of the lenses 710, 712 may be moved to ensure the focus of an object is placed on the active areas of the respective image sensors 704, 706 so to maintain a high quality stereoscopic image, which may be affected by a lateral distance between the image sensors 704, 706 as discussed above. A gap between the image sensors was discussed above, which led to moving the image sensors to maintain the gap. In this embodiment, however, the gap may be initially established when mounting the image sensors 704, 706 to the interposer 702 via bonds 708, but maintenance of the gap, which may change due to operating temperature for example, may be performed by moving the lenses 710,712.

FIG. 7B shows an example imaging sensor system 750 that may include windows 730 through the interposer 702 with the image sensors 704, 706 being mounted to the interposer 702 on one side and the actuators 714, 716 and lenses 710, 712 mounted to the interposer 702 on an opposite side. In this embodiment, light directed towards the image sensors 704, 706 may respective lenses 710, 712 may pass through the windows 730. Outside of the arrangement of the components and the inclusion of the windows 730, the system 750 may be substantially similar to the system 700, 500, and 300, and may similarly operate. While not shown in FIG. 7B, the actuators 714, 716 may each have an aperture 731 aligned with an optical path of the respective lenses 710, 712 that allows for the incident light to propagate through the lenses 710, 712, the actuators 714, 716, and be incident on an active area of the respective image sensors 704, 706.

The system 750 may include actuation controller 720 coupled to the actuators 714, 716 via connections 718. While a connection is not shown in FIG. 7B, the actuation controller 720 may be coupled to external control electronics via the interposer 702 similar to as shown in FIGS. 5 and 7A. The image sensors 704, 706 may be mounted to the interposer 702 by the bonds 708, which may be formed from self-aligning grooves. The actuators 714, 716 may also be mounted to the interposer 702 by connections 718, which may also be formed from self-aligning grooves.

In operation, one of the actuators 714, 716 may move their respective lenses 710, 712 based on control signals received from the actuation control 720. The movement of the lens(es) may be performed to calibrate the system 750, or perform super resolution imaging, or to maintain a desired gap between the image sensors 704, 706. The desired gap in this embodiment may be a lateral space between active areas of the image sensors 704, 706 that are receiving the incoming light from the lenses 710, 712, for example. If, for example, one or both of the image sensors 704, 706 move with respect to one another, the lenses 710, 712 may be moved by their respective actuators 714, 716 so that a desired gap between the active areas of the image sensors receiving the light is maintained.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus, comprising:
   an interposer including first and second windows and conductive conduits formed in or on the interposer, the first and second windows laterally spaced, and the conductive conduits to provide electrically conductive paths through the interposer;
   first and second image sensors disposed on the interposer across the first and second windows, respectively, and coupled to the conductive conduits, the first and second image sensors laterally spaced by a gap, wherein active areas of the first and second image sensors are each aligned to receive incident light through the first and second windows, respectively, wherein a perspective of the first image sensor is different than a perspective of the second image sensor based at least in part on the gap; and
   first grooves and ridges etched into a first bonding surface of the interposer and sized to mate with second grooves and ridges etched into second bonding surfaces of the first and second image sensors to align the first and second image sensors to the interposer and set the gap between the first and second image sensors on the interposer, wherein at least a portion of the first ridges includes a metal coating for forming mechanical or electrical connections to the first or second image sensors.

2. The apparatus of claim 1, further comprising first and second lenses disposed at least partially across the first and second windows, respectively, and arranged on an opposite side of the interposer as are the first and second image sensors, such that the interposer is disposed between the first and second image sensors and the first and second lenses.

3. The apparatus of claim 2, wherein the active areas of the first and second image sensors are positioned to be coincident with a focal plane of respective first and second lenses.

4. The apparatus of claim 2, wherein the first and second lenses direct incoming light through to the first and second image sensors through the first and second windows, respectively.

5. The apparatus of claim 2, further comprising:
   first and second actuators coupled to the interposer and each including an aperture aligned with a corresponding one of the first and second windows to pass the incident light through to the first and second image sensors, respectively.

6. The apparatus of claim 5, wherein the first and second lenses are disposed on the first and second actuators, respectively.

7. The apparatus of claim 5, further comprising:
   actuation controllers disposed in or on the interposer and coupled to the first and second actuators to control movement of the first and second actuators in one, two, or three directions.

8. The apparatus of claim 1, wherein the interposer and the first and second image sensors are formed from the same material.

9. The apparatus of claim 8, wherein the first and second image are front side illuminated or backside illuminated.

10. The apparatus of claim 1, wherein at least the interposer and the first and second image sensors form an imaging sensor system, wherein the imaging sensor system is included in an endoscope, and wherein a controller electrically couples to the first and second image sensors by the conductive paths formed through the interposer.

11. The apparatus of claim 1, further comprising:
   metal layers disposed in one or more of the first grooves between adjacent ridges etched into the interposer to form one or more bonding sites for forming electrical or mechanical connections to one or more second ridges of the first and second image sensors.

12. An apparatus, comprising:
   an interposer including an actuation controller embedded therein;
   first and second image sensors coupled to a surface of the interposer such that the first and second image sensors are physically distinct from the actuation controller embedded in the interposer, the first and second image sensors laterally separated by a gap such that the first image sensor has a different perspective than the second image sensor;

first and second actuators coupled to the interposer, the first and second actuators capable of movement in three directions, wherein the first actuator includes a first aperture and the second actuator includes a second aperture; and first and second lenses disposed on first and second surfaces of the first and second actuators, respectively, wherein a first optical axis of the first lens is aligned with the first aperture and a second optical axis of the second lens is aligned with the second aperture, wherein the first and second lenses are aligned with the first and second image sensors, respectively, to direct incident light onto active areas of the first and second image sensors through the first and second apertures, wherein the actuation controller is electrically coupled to the first and second actuators to electrically manipulate the first and second actuators.

13. The apparatus of claim 12, wherein the image sensors capture respective images for the generation of stereoscopic images.

14. The apparatus of claim 12, wherein the active areas of the first and second image sensors are incident with a focal plane of the respective first and second lenses.

15. The apparatus of claim 12, wherein the first and second actuators are coupled to the interposer with self-aligning bonds, and wherein the first and second image sensors are coupled to the interposer with self-aligning bonds.

16. The apparatus of claim 12, wherein the first and second lenses include one or more lenses, one or more optical filters, one or more polarizers, and combinations thereof.

17. The apparatus of claim 12, further comprising:
first and second windows disposed in the interposer, the first window aligned with the first image sensor and the first lens and the second window aligned with the second image sensor and the second lens.

18. The apparatus of claim 12, wherein the actuation controller includes logic that when executed by the actuation controller causes the apparatus to perform operations including:
receiving a first signal from at least one of the first and second image sensors, the signal including instructions for moving at least one of the first and second lenses using at least one of the first and second actuators; and
electrically manipulating at least one of the first and second actuators based on the first signal.

19. The apparatus of claim 18, wherein the actuation controller includes further logic that when executed by the actuation controller causes the apparatus to perform additional operations including:
receiving a second signal from an external controller; and
electrically manipulating at least one of the first and second actuators based on the second signal.

* * * * *